United States Patent [19]

McCune

[11] Patent Number: 4,691,738
[45] Date of Patent: Sep. 8, 1987

[54] CONTROL VALVE FOR USE WITH TOURNIQUET SYSTEM

[75] Inventor: William L. McCune, Denver, Colo.

[73] Assignee: Aspen Laboratories, Inc., Englewood, Colo.

[21] Appl. No.: 525,600

[22] Filed: Aug. 23, 1983

[51] Int. Cl.$^4$ .............................................. F16K 7/06
[52] U.S. Cl. .................................. 137/627.5; 128/327; 137/595; 137/596; 137/597; 137/636.1; 251/9
[58] Field of Search ............ 137/595, 596, 863, 627.5, 137/636.1, 597; 251/6, 7, 10, 9, 263; 128/327; 417/474, 479

[56] References Cited

U.S. PATENT DOCUMENTS

| | | | |
|---|---|---|---|
| 1,259,520 | 3/1918 | Jenkins | 251/263 X |
| 2,182,724 | 12/1939 | Hennessy | 137/597 X |
| 2,529,794 | 11/1950 | Brown | 251/263 X |
| 2,594,762 | 4/1952 | Freund et al. | 137/597 X |
| 3,038,449 | 6/1962 | Murphy, Jr. et al. | 137/597 X |
| 3,450,152 | 6/1969 | Ouellette | 251/9 X |
| 3,754,768 | 8/1973 | Ellis et al. | 251/9 X |
| 3,825,008 | 7/1974 | Shook | 128/327 |
| 3,918,490 | 11/1975 | Goda | 137/597 |
| 4,061,142 | 12/1977 | Tuttle | 251/9 X |
| 4,282,902 | 8/1981 | Haynes | 137/595 X |
| 4,294,261 | 10/1981 | Baker et al. | 128/691 |
| 4,321,929 | 3/1982 | Lemelson et al. | 128/630 |
| 4,328,834 | 5/1982 | Oates, Sr. et al. | 251/9 X |
| 4,573,888 | 3/1986 | Kitchin | 417/560 |

FOREIGN PATENT DOCUMENTS

| | | | |
|---|---|---|---|
| 952782 | 8/1974 | Canada | 128/119 |
| 2902356 | 7/1980 | Fed. Rep. of Germany . | |
| 2477867 | 3/1980 | France . | |
| 240423 | 8/1969 | U.S.S.R. | 251/9 |

Primary Examiner—Martin P. Schwadron
Assistant Examiner—Stephen M. Hepperle
Attorney, Agent, or Firm—Margaret L. Geringer

[57] ABSTRACT

This invention relates to a new control valve intended to be used to control the supply and exhaust of fluids to a dual tourniquet system. The tubes supplying and exhausting the tourniquets are of a flexible nature, and as such may be squeezed to stop the flow of fluids therethrough. The inventive valve includes cam members with camming projections formed thereon at various predetermined positions on the circumferences thereof. Simultaneous rotation of the cam members by a control knob results in sequential filling and emptying of the tourniquets in a predetermined sequence. The valve is especially useful in the practice of the Bier block procedure.

11 Claims, 8 Drawing Figures

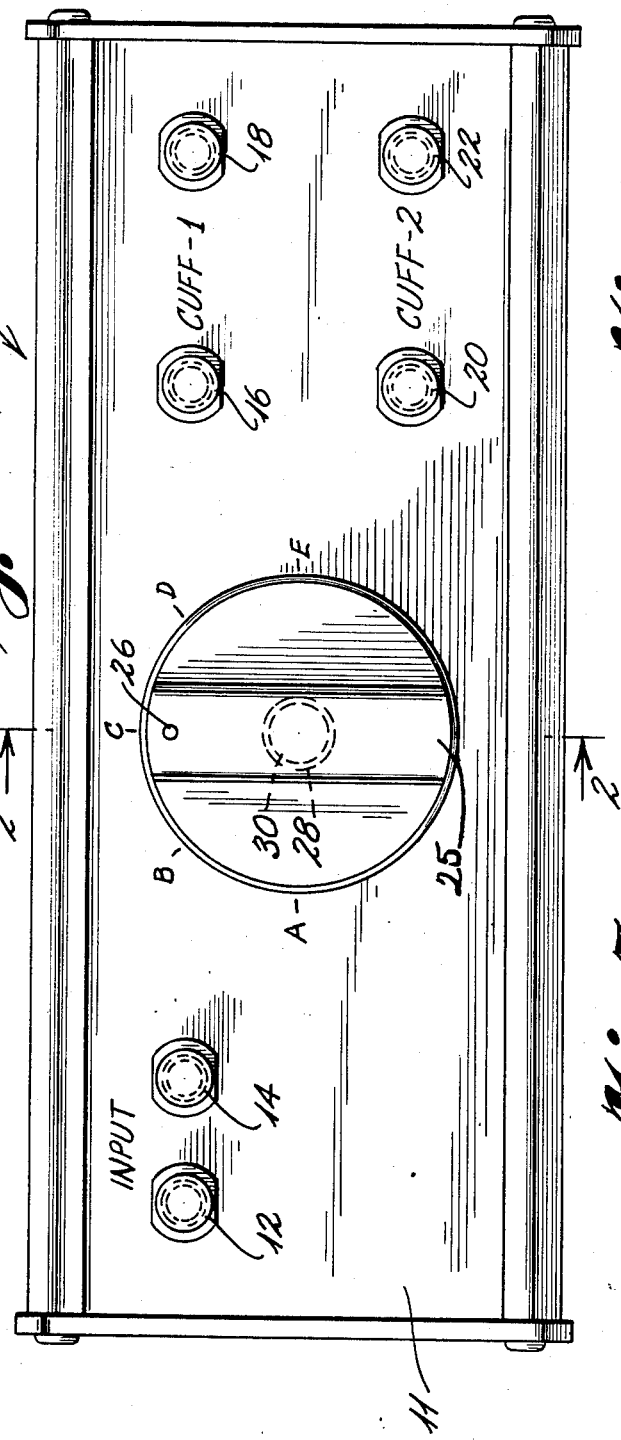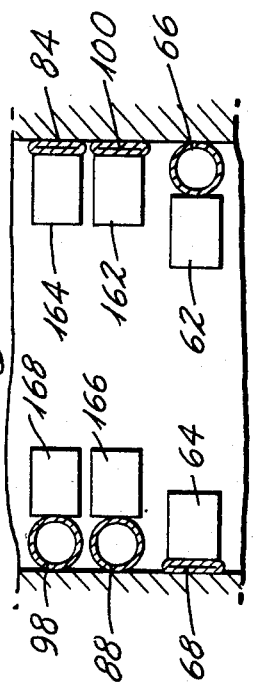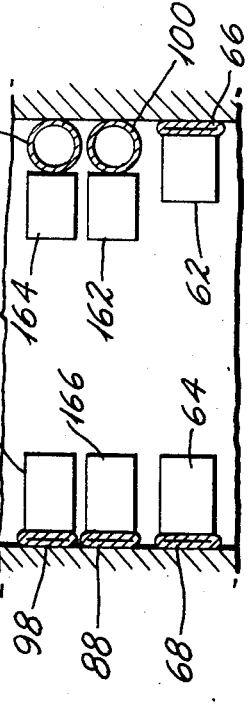

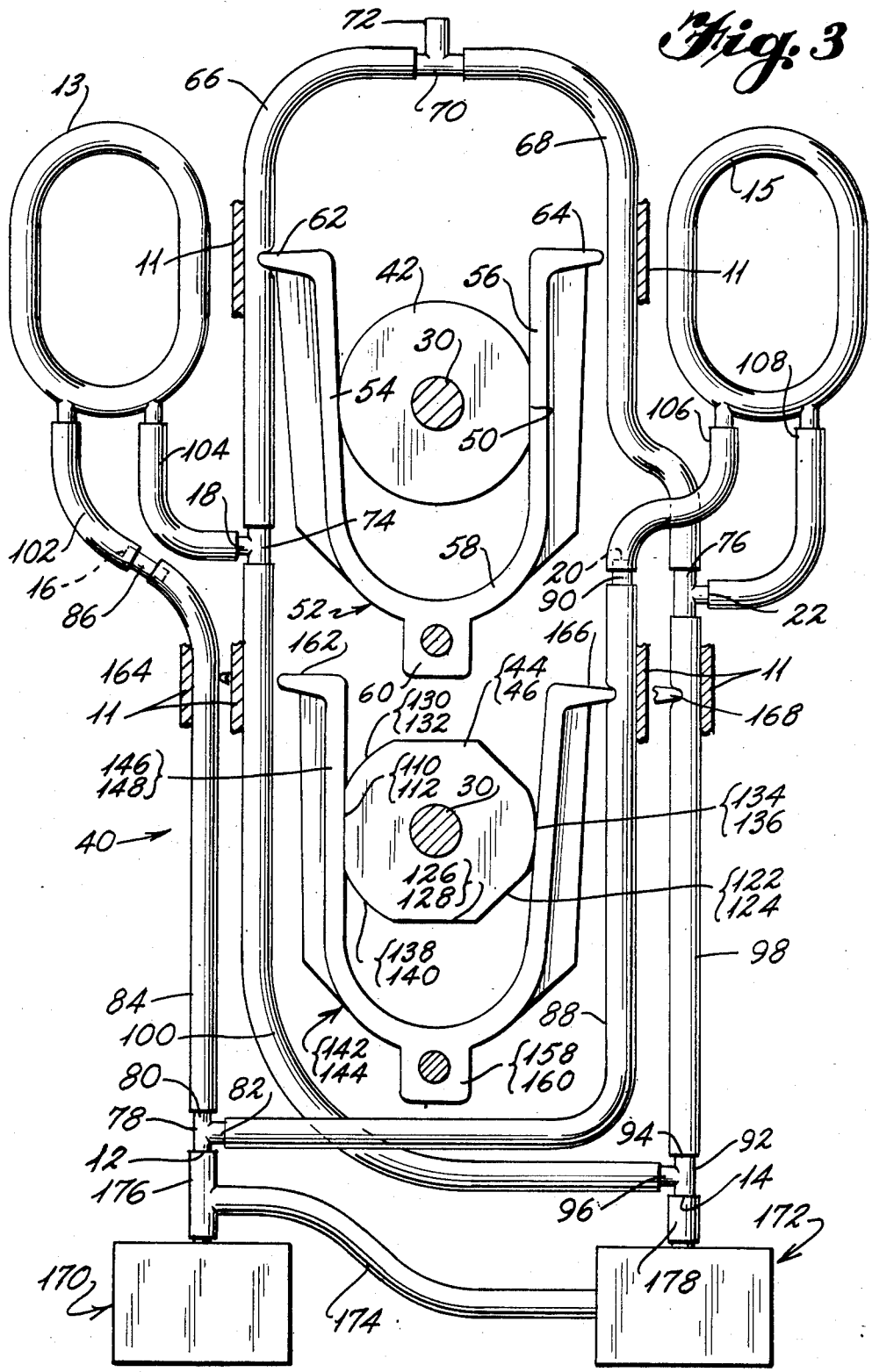

CONTROL VALVE FOR USE WITH TOURNIQUET SYSTEM

BACKGROUND OF THE INVENTION

The present invention relates to a control valve for use in controlling supply and exhaust of fluid to and from a tourniquet system. Control valves generally of the type disclosed herein and valves for controlling tourniquet systems in general are known in the art. Applicant is aware of the following documents generally pertinent to the structure of the valve disclosed herein:

U.S. Pat No. 3,918,490 to Goda discloses a valve for controlling flow between a plurality of inlets and a lesser plurality of outlets. As shown in FIG. 3, each outlet is associated with two inlets. Each valve comprises a cam 50 with a flat surface which, when facing a respective tube 45 or 46, allows flow therepast.

U.S. Pat. No. 4,061,142 to Tuttle shows a valve in FIG. 2 thereof in which a cam 24 acts through biasing springs 28 and 29 to pivot levers 26 and 27 respectively. The levers 26 and 27 have extensions 43 and 44 respectively which engage parallel tubes at 41 and 42 respectively. Thus rotation of the cam member 24 controls the flow of fluid through the tubes.

U.S. Pat. No. 4,282,902 to Haynes discloses a valve for controlling flow of fluid in a series of flexible tubes. As shown in FIG. 3, representative of the invention, a pair of tubes are controlled by cam member a, the rotation of which flexes the levers 16a and 16j to thereby open and close the respective tubes B1 and B5.

U.S. Pat. No. 4,328,834 to Oates, Sr., et al. shows a single valve for controlling fluid flow in two tubes 14 and 16. The valve includes pivoted lever and cam actuator 40.

U.S.S.R. Pat No. 240,423 shows a valve for controlling the flow from one inlet to one of two outlets. The valve includes cam 2 which acts upon levers including projections 3 and 4 formed thereon to control the flow through outlet tubes 9 and 10.

Other patents generally pertinent to the valve aspect of the present invention but less pertinent than the above discussed references are:

U.S. Pat. No. 1,879,631 to Mott, et al.,
U.S. Pat. No. 2,996,081 to Wise,
U.S. Pat. No. 3,134,403 to Rudelick, and
German Pat. No. 2,902,356 to Simens.

It is noted that none of the above discussed references shows the concept of a cam actuated supply and exhaust valve operating by the compression of supply and exhaust tubes.

Applicant is further aware of the following documents which are generally pertinent to the concept of controlling flow to a tourniquet system:

U.S. Pat. No. 3,167,067 to Rand discloses a system for controlling inflation and deflation of four tourniquets located on the extremities. The system sequentially keeps three of the four tourniquets inflated while the fourth is exhausted. As motor 28 rotates shaft 26, the valve sequentially inflates the deflated tourniquet while deflating one of the three previously inflated tourniquets.

U.S. Pat. No. 3,465,749 to Moreland, et al. discloses a rotating tourniquet system including the valving of Rand, and with the further provision of pressure relief valving to prevent excess pressure in the four tourniquets.

U.S. Pat. No. 3,825,008 to Shook shows in FIG. 4, a pair of tourniquets 19 and 19a which are alternately inflated for effecting the "Bier block." The control of the inflation of the tourniquets 19 and 19a is by manually operated toggle valves 35 and 35a.

U.S. Pat. No. 4,321,929 to Lemelson, et al. discloses a system for controlling the inflation and deflation of tourniquets 11 and 15 for a leg and arm respectively. Various disclosed body condition sensors control the inflation and deflation of the tourniquets.

Other documents pertinent to the combination subject matter of means for controlling the inflation and or deflation of tourniquets or inflatable cuffs are known to applicant and are listed below:

U.S. Pat. No. 1,147,560 to Shurtleff,
U.S. Pat. No. 3,826,249 to Lee, et al.,
U.S. Pat. No. 3,862,629 to Rotta,
U.S. Pat. No. 4,013,069 to Hasty,
U.S. Pat. No. 4,039,039 to Gottfried,
U.S. Pat. No. 4,202,325 to Vellari, et al.,
U.S. Pat. No. 4,294,261 to Baker, et al.,
Canadian Pat. No. 952,782 to Gottfried, et al., and
French Pat. No. 2,477,867 to Piedelivre.

It is noted that none of the above discussed patents discloses a cam actuated supply and exhaust valve which compresses supply and exhaust tubes to control the inflation and deflation of plurality of tourniquets.

SUMMARY OF THE INVENTION

The instant invention may be characterized in terms of two broad aspects. In a first aspect, the invention includes a valve for controlling the supply and exhaust of fluid to a plurality of tourniquets. The valve is generally of the tube compressor type, and includes a structure for controlling the flow through a plurality of flow lines in a predetermined sequence. The flow lines comprise flexible tubes which are conducted into the valve housing. The valve includes a valve member which comprises a trio of cam members. Two of the cam members control the supply of fluid from a pressure source to both tourniquets, whereas a third cam member controls the exhausting of fluid from the tourniquets. The cam members are rigidly mounted together and rotation of a single knob controls the rotation of all three cam members simultaneously.

In the preferred embodiment, rotation of the knob to sequential stop positions sequentially causes: first pressurization of a first tourniquet and exhausting of a second tourniquet, then holding of the first tourniquet at its pressure level while pressurizing the second tourniquet, then exposing both the first and the second tourniquets to inlet pressure, then exposing of the first tourniquet to the pressure while holding the second tourniquet at its pressurized level, and than finally exhausting the first tourniquet while exposing the second tourniquet to inlet pressure.

This valving sequence is specifically designed to allow the use of the Bier block procedure. In this procedure, two tourniquets are put on the limb which is to be anesthetized and the proximal tourniquet is inflated, that is the tourniquet closest to the heart. The limb is than anesthetized, and after the anesthesia takes effect and the first tourniquet becomes painful, the distal tourniquet, that is the tourniquet most distant from the heart, is inflated and the proximal tourniquet is deflated. In this way, the distal tourniquet is inflated on an area of the limb which has been anesthetized and as such, such inflation of the tourniquet is painless. In a further aspect, this procedure prevents the anesthetic from travelling beyond the area of the limb desired to be anesthetized.

The second aspect of the present invention involves the combination of the valve above described with the tourniquets and the associated conduits which in combination comprise a tourniquet system including the means for controlling the inflation and deflation thereof. The system includes a pair of tourniquets connected into the above described supply and exhaust flow lines which are inflated and deflated by a source of pressure in accordance with the sequence of movement of the control valve as described above. A pressure monitor monitors the pressures in the various conduits of the system and exercises control over the source of pressure.

Accordingly, it is a first object of the present invention to provide an improved valve.

It is a further object of the present invention to provide an improved valve which will sequentially control flow through a plurality of flow lines in a predetermined sequence.

It is a still further object of the present invention to provide an improved valve which utilizes cam members to controllably valve a plurality of flexible flow lines.

It is yet a still further object of the present invention to provide a valve with pivoting members interposed between cam members and flexible tubes to transmit the projections on the cam members to the appropriate flexible tubes.

It is a further object of the present invention to provide a system for inflating tourniquets which uses the abovenoted control valve.

It is a yet further object of the present invention to provide a system including two tourniquets, the inflation and deflation of which are controlled by such control valve.

It is a still further object of the present invention to provide a system which allows the performance of the procedure known as the Bier block procedure.

These and other objects, features and advantages of the invention will become more readily apparent from the following detailed description when taken in conjunction with the accompanying drawings.

BRIEF DESCRIPTION OF THE DRAWINGS

FIG. 1 shows a top view of the inventive valve and control box including a view of the control knob thereof.

FIG. 3 shows a schematic view of the inventive valve in its environment of intended use.

FIGS. 4, 5, 6, 7 and 8 show, respectivley, the orientations of the foot portions of the respective U-shaped pivoting members with respect to their associated tubes, for positions A, B, C, D and E, respectively, of the control knob of FIG. 3.

SPECIFIC DESCRIPTION OF THE PREFERRED EMBODIMENTS

Figure 2:
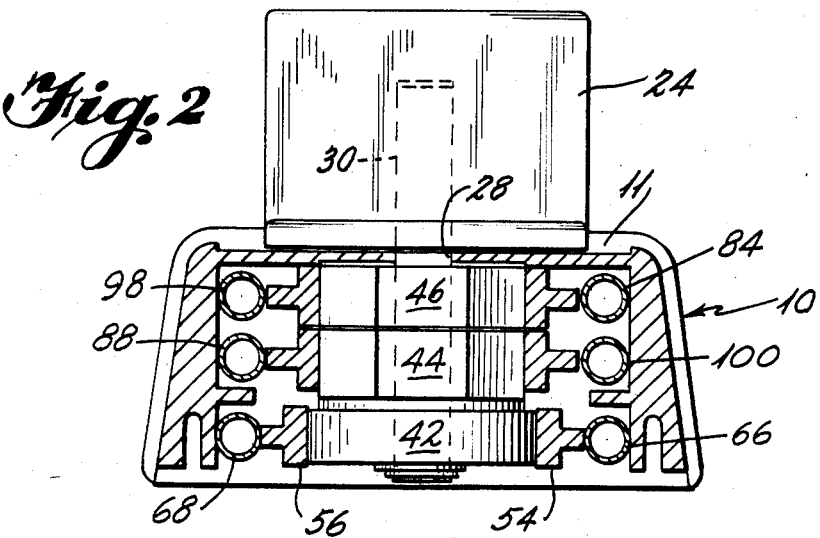
FIG. 2 shows a cross sectional view along the line 2—2 of FIG. 1.

Referring first to FIG. 1, the inventive valve is housed, in the preferred embodiment, in a housing 10. The housing 10 includes a face 11 on which are orientated inputs 12 and 14, outputs 16 and 18 to a first tourniquet cuff, and outputs 20 and 22 to a second tourniquet cuff. The face 11 further includes a hole 28 (shown in phantom) through which extends valve stem 30 (also shown in phantom) which is rigidly attached to the operative structure of the inventive valve. Selector knob 24 is fixedly attached in a manner well known in the art to the stem 30 and includes, in the preferred embodiment, an upstanding rib 25 and a dot 26 indicative of the position of the valve. Also located on the face 11 are indicia shown in FIG. 1 as the letters A, B, C, D and E. These indicia, when lined up with the dot 26, indicate the position of the valve within the housing 10.

Referring now to FIGS. 2 and 3, the valve 40 is seen to include three stacked cam members 42, 44 and 46. The cam 42 is of generally circular shape including substantially circular periphery 48 and a chord-like flat portion 50 extending approximately ⅛th the circumference of the cam 42. A U-shaped pivoting member 52 includes legs 54 and 56 on opposite sides of the cam 42 and a connecting portion 58 which includes a portion 60 which is mounted in a fixed position within the housing 10 by fastening means not shown. The leg 54 includes a foot 62 whereas the leg 56 includes a foot 64. The feet 62 and 64 act as valve members compressing associated tubes 66 and 68 at preselected rotative positions of cam 42 to thereby valve the tubes 66 and 68.

In the preferred embodiment, the feet 62 and 64 comprise exhaust valves which control, respectively, the exhausting of tourniquet cuffs 13 and 15. A T-shape coupling member 70 connects the extremities of tubes 66 and 68 and includes an outlet 72 to atmosphere. The tube 66 at its other end is connected to a T-shaped coupling 74 which coupling integrally includes the above described outlet port 18 to the first tourniquet cuff 13. The tube 68 at its other end is connected to another T-shaped coupling 76 which integrally includes the above described outlet port 22 to the second tourniquet cuff 15. Input port 12 is formed as a part of a further T-shaped coupling 78 which includes two outlets 80 and 82. Outlet 80 is connected by tube 84 with coupling 86 which includes as an outlet the outlet port 16 to the first tourniquet cuff 13. Outlet 82 of the coupling 78 connects with coupling member 90 through flexible tube 88. The coupling 90 includes as an outlet the outlet port 20 to the second tourniquet cuff 15. T-shaped coupling 92 has an inlet thereof the input port 14 and includes outlets 94 and 96. The outlet 94 connects with the coupling 76 through tube 98 whereas the outlet 96 connects with coupling 74 through tube 100. Outlets 16 and 18 connect with the first tourniquet cuff 13 through respective tubes 102 and 104, whereas outlets 20 and 22 connect with second tourniquet cuff 15 through flexible tubes 106 and 108 respectively.

As shown in FIG. 2, the cams 44 and 46 may be separate entities. Referring to FIG. 1, the cams 44 and 46 have identical circumferential configurations and, as such, may be comprised of a single cam of twice the thickness as the cam 42 if desired. The cams 44 and 46 are formed, as is the cam 42, of cylindrical disks. The cam 44 includes flat surfaces 110, 114, 118, 122 and 126 machined out of the circular outer periphery of the cam 44. These flat surfaces leave as the remainder of the circular periphery of the cam 44 circular cam surfaces 130, 134 and 138. In corresponding fashion, the cam 46 includes flat surfaces 112, 116, 120, 124 and 128, and circular surfaces 132, 136 and 140. U-shaped pivoting members 142, 144 are substantially identical in construction to the U-shaped pivoting member 52. The member 142 includes legs 146 and 150, feet 162 and 166, and U-shaped connecting portion 154 which includes pivot portion 158 connected with the same fastening member as the pivoting point 60 of the U-shaped pivoting member 52. Correspondingly, the U-shaped pivoting member 144 includes legs 148 and 152, feet 164 and 168, U-shaped connecting portion 156 and pivoting portion 160 corresponding to the pivoting portions 158 and 60. If desired, members 142, 144 could be made as a single member of double the thickness as the pivoting member 52.

The cams, leg and foot portions of the U-shaped pivoting members, and associated tubes are so configured that whenever a flat surface of a respective cam is resting against a respective leg, the associated tube is unrestricted, whereas whenever a circular shaped portion of a respective cam is an engagement with a respective leg, the associated tube is compressed to prevent flow therethrough through pressure applied thereon by the foot which is attached to the leg on which is engaged the circular portion of the cam. As shown in FIG. 3, a pressure source 170, usually a pump, is connected to the input 12 whereas a pressure monitor 172 is connected to the input 14. The pressure source 170 supplies pressure for inflation of the two tourniquet cuffs 13 and 15 whereas the pressure monitor 172 monitors the pressures in the various tubes and thereby controls the operation of the pressure source 170. A sensing line 174 is connected in the conduit 176 from the pressure source to the inlet 12 and monitors the output pressure of the pump at that point. The pressure monitor senses the pressure in the lines 174 and 178. As long as these two pressures are substantially equal, the pressure monitor 172 will control the pressure source 170 to inflate the cuffs 13 and 15 to the desired predetermined pressure. Whenever the pressure difference between the lines 174 and 178 exceeds a predetermined amount, for example, 20 to 30 millimeters of mercury, this tells the pressure monitor 172 that there is a malfunction in the system whether it be a leak in one of the cuffs 13 and 15, or a leak or kink in one of the various flexible tubes. In this instance of differential pressure between lines 174 and 178 exceeding the predetermined amount, the pressure monitor will sound an alarm (not shown) and deactivate the pressure source 170. If desired, the connections of the pressure source 170 and the pressure monitor 172 may be reversed without altering system operation. In this situation, the pressure source 170 would be connected to line 178 and input 14 whereas the pressure monitor 172 would be connected to line 176 and input 12. Sensing line 174 would be tapped into line 178 to sense the pressure downstream of pressure source 170. In the preferred embodiment, the pressure source 170 comprises a diaphragm pump including flexible check valves for supply and exhaust. This pump is the subject U.S. Pat. No. 4,573,888, to Kitchen, which is assigned to Aspen Laboratories. Inc.

FIGS. 4–8 depict the positions of the feet 62, 64, 162, 166, 164 and 168 with respect to the positions of their respective flexible tubes 66, 68, 100, 88, 84 and 98. As explained above, the position of the various feet is determined by the engagement of the various cam faces with the respective legs of the U-shaped pivoting members. It is important to note that the U-shaped pivoting members 52, 142 and 144 are made of a rigid but resilient material. In the preferred embodiment, the U-shaped pivoting members may be made of plastic. These U-shaped pivoting members are fixed to the housing 10 as stated above at the points 60, 158 and 160. The U-shaped pivoting members do not pivot about these points 60, 158 and 160 but instead the legs of the U-shaped pivoting members flex with respect to the respective connecting portions 58, 154, 156 under the forces imparted to them from the cams to resiliently move the respective feet in a direction to close or open the associated tubing.

Figure 4:
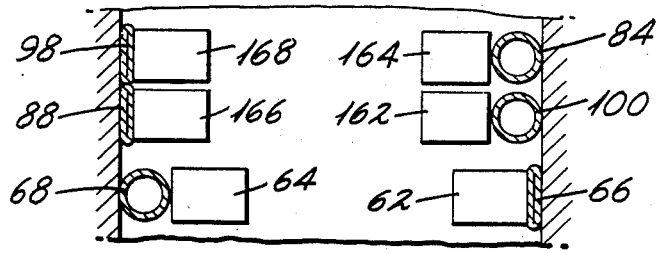

FIG. 4 depicts the positions of the various feet as related to their respective tubings for the position of valve selector knob 24 shown in FIG. 3 (position A) and for the schematic configuration of the circuit shown in FIG. 1. More particularly, the figure shows exhaust port 66 from the first cuff 13 closed by the foot 62, tubes 84 and 100 supplying and monitoring respectively the first cuff 13 are opened, the exhaust tube 68 from the cuff 15 is opened and the tubes 88 and 98 supplying and monitoring the second cuff 15 are closed. In this mode, the pressure source 170 will fill the first cuff 13 with fluid while the pressure monitor 172 will monitor such filling. In this position, the pressure source 170 is isolated from the second cuff 15 which is exhausted to the atmosphere through line 68 and port 72.

Figure 5:
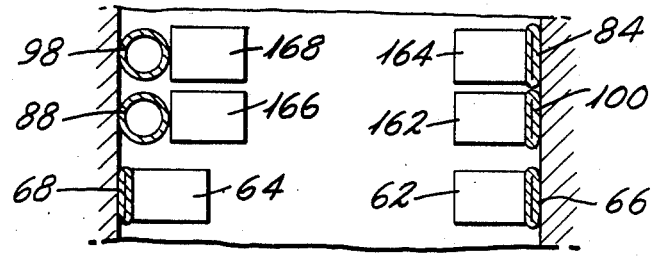

FIG. 5 shows the orientation of the feet with respect to the associated tubing for the valve selector knob 24 position B shown in FIG. 3. In this position, tubes 84 and 100 are isolated from the pressure source and the tube 66 is sealed from the exhaust ports 72. In this way, any pressurized fluid within the first cuff 13 is isolated therein. Meanwhile the exhaust tubing 68 from the second cuff 15 is closed by foot 64 whereas tubes 88 and 98 supplying and monitoring, respectively, the cuff 15 are fluidly opened to the pressure source 170 and pressure monitor 172 respectively. In this mode, the second cuff 15 is pressurized and monitored while the first cuff 13 is isolated from both the pressure source and the pressure monitor.

Figure 6:
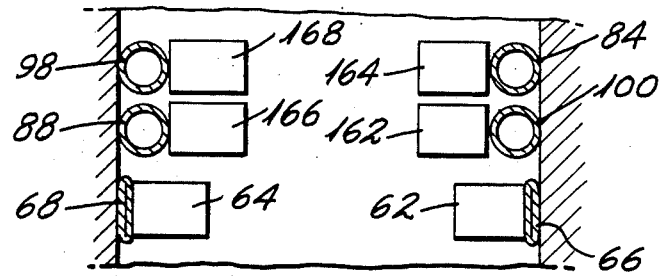

FIG. 6 depicts the position of the feet with respect to their associated tubing for valve selector knob 24 position C. In this configuration, both the cuffs 13 and 15 are fluidly connected to the pressure source 170 and the pressure monitor 172 while the exhaust passages 66 and 68 from the cuffs 13 and 15, respectively, are sealed off by respective feet 62 and 64. In this configuration, both of the cuffs 13 and 15 are pressurized by the pressure source 170 and monitored by the pressure monitor 172 simultaneously.

FIG. 7 depicts the orientation of the feet with respect to their tubes for position D of the valve selector knob 24. In this position, the second cuff 15 is isolated from both the pressure source 170 and the pressure monitor 172 as well as from the exhaust 72. Further, the first cuff 13 is fluidly connected to the pressure source 170 and pressure monitor 172 while its exhaust passage 66 is isolated from the exhaust port 72 by the foot 62. In this configuration, the first cuff 13 is pressurized by the pressure source 170 and monitored by the pressure monitor 172 while the fluid pressure within the second cuff 15 is isolated from both the supply and the exhaust.

FIG. 8 shows the configuration of the feet for position E of the valve selector knob 24. In this position, the first cuff 13 is exhausted by tube 66 and exhaust port 72 while simultaneously being isolated from the pressure source 170 and monitor 172. Meanwhile, the second cuff 15 is fluidly connected to the pressure source 170 and the pressure monitor 172 through tubes 88 and 98 while exhaust passage 68 is sealed off by foot 64. In this configuration, the second cuff 15 is pressurized by the pressure source 170 and monitored by the pressure monitor 172 while the first cuff 13 is exhausted.

By sequentially turning the valve selector knob 24 through positions A, B, C, D and E while pausing at each position, a physician or technician may safely and accurately practice the Bier block technique. More particularly, in position A, the first cuff 13 is inflated by the pressure source 170 and monitored by the pressure monitor 172 while the second cuff 15 is deflated. In this case, the first cuff 13 corresponds to the proximal tourniquet and the second cuff 15 corresponds to the distal tourniquet. After the pressure monitor 172 indicates that the first cuff 13 has stabilized at the predetermined pressure, the limb is anesthetized. After awhile, the first cuff 13 corresponding to the proximal tourniquet becomes painful to the patient. At this point valve selector knob 24 is turned to position B. In this position, the first tourniquet is held at its present pressure while the second tourniquet corresponding to the cuff 15 is pressurized and monitored. When the pressure monitor 172 indicates that the second cuff 15 has been properly pressurized, valve selector knob 24 is then turned to position C. In position C, both the first cuff 13 and the second cuff 15 corresponding, respectively, to the proximal and distal tourniquets are exposed to the pressure source 170 and their pressure is monitored by the pressure monitor 172. When the pressure monitor 172 indicates that the pressure in the cuffs 13 and 15 has stabilized at the predetermined pressure, valve actuator 24 is turned to position D. In position D, the first cuff 13 is exposed to the pressure source 170 and monitored by the pressure monitor 172 while the second cuff 15 is held at its present pressure and isolated from both the pressure source and the pressure monitor as well as the exhaust port 72. When the pressure monitor 172 indicates that the pressure in the first cuff 13 has stabilized that the predetermined level the valve actuator knob 24 is than turned to position E. In position E, the second cuff 15 is exposed to the pressure source 170 and monitored by the pressure monitor 172 while the pressure in the first cuff 13 is exhausted through the port 72. Again, in this way, the distal tourniquet is inflated on an area of the limb which has been anesthetized and as such, such inflation of the tourniquet is painless. As stated earlier, this procedure presents the anesthetic from travelling beyond the area of the limb desired to be anesthetized.

It is stressed herein, that the present invention may be used in any sequence of actuations of the valve selector knob 24 to provide whatever results are desired. For example, if it is desired to simultaneously inflate both of the cuffs 13 and 15, the operator merely turns the valve selector knob 24 to position C (FIG. 6). Again, in position C, both cuffs 13 and 15 will be pressurized and monitored simultaneously. Further, for example, if one wishes merely to inflate the cuff 15, the valve selector knob 24 is turned to position E (FIG. 8) wherein the cuff 15 will be pressurized and monitored simultaneously. Again, it is stressed, that the pressure source 170 and pressure monitor 172 may be attached to the respective inputs 12 and 14 either in an orientation shown in FIG. 1 or in a reverse orientation. If their orientation is reversed from the position shown in FIG. 3, the conduit 174 would similarly be reversed so that it would connect the pressure monitor 172 with the conduit 178 attached to the input 14. The sequences of actuations of the valve 40 through its actuator knob 24 are only limited by the imagination of the operator and the reliability and fail safe way in which the instant invention both supplies and exhausts while monitoring a pair of cuffs is unmatched in the prior art. Obviously, the valve could be used in many other enviroments. Instead of the cuffs 13 and 15 the outputs could be connected to any sealed containers or flow systems wherein close pressure monitoring is desired. Further, the valve could be used, if desired, to control the supply and exhaust while monitoring of a single enclosure. Other modifications will be evident to those skilled in the art and these, too, are intended to fall within the scope of the invention. The presently disclosed embodiment is therefore to be considered in all respects as illustrative and not restrictive, the scope of the invention being defined solely by the appended claims rather than by the foregoing description, and all changes which come within the meaning and range of equivalency of the claims are therefore intended to be embraced therein.

I claim:

1. In a valve including a housing with:
   (a) first and second inlets;
   (b) first and second outlets;
   (c) a first flexible conduit fluidly connecting said first inlet with said first outlet;
   (d) a second flexible conduit fluidly connecting said second inlet with said second outlet;
   (e) first and second valve means for controlling flow through the respective first and second conduits, said first and second valve means each including:
      (i) rotatable cam means, and
      (ii) pivoting means interposed between said cam means and the respective flexible conduit;
      (iii) rotation of said cam means causing pivoting of said pivoting means to sequentially compress and release said flexible conduit, the improvement wherein, said pivoting means for said first and second valve means comprising a single U-shaped member mounted in surrounding relation to said cam means, a first leg of said U-shaped member comprising said first valve means pivoting means, a second leg of said U-shaped member comprising said second valve means pivoting means and a further portion of said U-shaped member integrally connecting said first and second legs together and wherein said cam means are located between said first and second legs and each said leg includes a foot extending outwardly therefrom, each said foot engaging a respective flexible conduit and selectively compressing or releasing said respective flexible conduit, and wherein said cam means are located between said further portion and each said foot, and wherein said further portion is rigidly connected to said housing and said first and second legs pivot with respect to said further portion, and wherein said first and second legs and said further portion are integrally formed in one piece from a resilient material, said material inherently resisting said pivoting of said first and second legs.

2. In a valve including a housing with:
   (a) first and second inlets;
   (b) first and second outlets;
   (c) a first flexible conduit fluidly connecting said first inlet with said first outlet;
   (d) a second flexible conduit fluidly connecting said second inlet with said second outlet;

(e) first and second valve means for controlling flow through the respective first and second conduits, said first and second valve means each including:
  (i) rotatable cam means, and
  (ii) pivoting means interposed between said cam means and the respective flexible conduit;
  (iii) rotation of said cam means causing pivoting of said pivoting means to sequentially compress and release said flexible conduit, the improvement wherein, said pivoting means for said first and second valve means comprising a single U-shaped member mounted in surrounding relation to said cam means, a first leg of said U-shaped member comprising said first valve means pivoting means, a second leg of said U-shaped member comprising said second valve means pivoting means and a further portion of said U-shaped member integrally connecting said first and second legs together and wherein said cam means are located between said first and second legs and each said leg includes a foot extending outwardly therefrom, each said foot engaging a respective flexible conduit and selectively compressing or releasing said respective flexible conduit, and wherein said cam means are located between said further portion and each said foot, and wherein said further portion is rigidly connected to said housing and said first and second legs pivot with respect to said further portion, and wherein said first and second legs and said further portion are integrally formed in one piece from a resilient material, said material inherently resisting said pivoting of said first and second legs, wherein said further portion is curved and includes a tab projecting from a periphery thereof, said tab being rigidly connected to said housing.

3. The invention of claim 1, wherein said cam means comprise a single cam menber with a plurality of cam projections extending outwardly therefrom, rotation of said cam member causing said cam projections to pivot said first and second legs outwardly to thereby cause each said foot to compress or release a respective flexible conduit in a predetermined sequence.

4. The invention of claim 1, further including:
  (a) third and fourth inlets;
  (b) third and fourth outlets;
  (c) a third flexible conduit fluidly connecting said third inlet and said third outlet;
  (d) a fourth flexible conduit fluidly connecting said fourth inlet and said fourth outlet;
  (e) third and fourth valve means for controlling flow through the respective third and fourth conduits, said third and fourth valve means each including:
    (i) rotatable cam means, and
    (ii) pivoting means interposed between said cam means and the respective flexible conduit;
    (iii) said cam means of said third and fourth valve means being mounted rigidly on a common actuation shaft with said cam means of said first and second valve means for simultaneous rotation therewith.

5. The invention of claim 4, wherein said cam means for said first and second valve means comprises a single first cam member and said cam means for said third and fourth valve means comprises a single second cam member.

6. The invention of claim 5, wherein said first and fourth flexible conduits comprise flow branches from a first pipe and said second and third flexible conduits comprise flow branches from a second pipe.

7. The invention of claim 6, wherein said first and third flexible conduits are fluidly connected to a first container and said second and fourth flexible conduits are fluidly connected to a second container.

8. The invention of claim 7, wherein said first conduit connects with a fifth flexible conduit downstream of said first valve means and upstream of said first container, said fourth conduit connects with a sixth flexible conduit downstream of said fourth valve and upstream of said second container, said fifth and sixth conduits connecting said first and fourth conduits, respectively, with the atmosphere, and fifth valve means for controlling flow through said fifth conduit and sixth valve means for controlling flow through said sixth conduit.

9. The invention of claim 8, wherein said fifth and sixth valve means comprise cam means rotatably engaging pivoting means and rigidly mounted on said common actuation shaft, rotation of said common actuation shaft in a predetermined sequence operating said first, second, third, fourth, fifth and sixth valve means to supply, isolate and exhaust said first and second containers in a predetermined sequence.

10. In a valve including a housing with:
  (a) first and second inlets;
  (b) first and second outlets;
  (c) a first flexible conduit fluidly connecting said first inlet with said first outlet;
  (d) a second flexible conduit fluidly connecting said second inlet with said second outlet;
  (e) first and second valve means for controlling flow through the respective first and second conduits, said first and second valve means each including:
    (i) rotatable cam means, and
    (ii) pivoting means interposed between said cam means and the respective flexible conduit;
    (iii) rotation of said cam means causing pivoting of said pivoting means to sequentially compress and release said flexible conduit, the improvement wherein, said pivoting means for said first and second valve means comprising a single U-shaped member mounted in surrounding relation to said cam means, a first leg of said U-shaped member comprising said first valve means pivoting means, a second leg of said U-shaped member comprising said second valve means pivoting means and a further portion of said U-shaped member integrally connecting said first and second legs together, and wherein said further portion is rigidly connected to said housing and said first and second legs pivot with respect to said further portion, and wherein said first and second legs and said further portion are integrally formed in one piece from a resilient material, said material inherently resisting said pivoting of said first and second legs.

11. In a valve including a housing with:
  (a) first and second inlets;
  (b) first and second outlets;
  (c) a first flexible conduit fluidly connecting said first inlet with said first outlet;
  (d) a second flexible conduit fluidly connecting said second inlet with said second outlet;

(e) first and second valve means for controlling flow through the respective first and second conduits, said first and second valve means each including:
   (i) rotatable cam means, and
   (ii) pivoting means interposed between said cam means and the respective flexible conduit;
   (iii) rotation of said cam means causing pivoting of said pivoting means to sequentially compress and release said flexible conduit, the improvement wherein, said pivoting means for said first and second valve means comprising a single U-shaped member mounted in surrounding relation to said cam means, a first leg of said U-shaped member comprising said first valve means pivoting means, a second leg of said U-shaped member comprising said second valve means pivoting means and a further portion of said U-shaped member integrally connecting said first and second legs together, and wherein said further portion is rigidly connected to said housing and said first and second legs pivot with respect to said further portion, and wherein said first and second legs and said further portion are integrally formed in one piece from a resilient material, said material inherently resisting said pivoting of said first and second legs, wherein said further portion is curved and includes a tab projecting from a periphery thereof, said tab being rigidly connected to said housing.

* * * * *